(12) United States Patent
Lipow (10) Patent No.: US 7,991,509 B2
(45) Date of Patent: Aug. 2, 2011

(54) AUGMENTED SURGICAL INTERFACE

(75) Inventor: Kenneth I. Lipow, Bridgeport, CT (US)

(73) Assignee: Kenneth I. Lipow, Bridgeport, CT (US)

( * ) Notice: Subject to any disclaimer, the term of this patent is extended or adjusted under 35 U.S.C. 154(b) by 1173 days.

(21) Appl. No.: 11/249,041

(22) Filed: Oct. 12, 2005

(65) Prior Publication Data

US 2006/0155263 A1    Jul. 13, 2006

Related U.S. Application Data

(60) Provisional application No. 60/617,864, filed on Oct. 12, 2004.

(51) Int. Cl.
*A61B 19/00* (2006.01)
*G05B 15/00* (2006.01)

(52) U.S. Cl. ............... 700/264; 700/245; 901/2; 606/1; 606/130

(58) Field of Classification Search ............... 901/2, 27; 700/245, 247, 264; 600/102, 104, 109; 606/1, 606/130
See application file for complete search history.

(56) References Cited

U.S. PATENT DOCUMENTS

| | | | |
|---|---|---|---|
| 5,943,914 A | 8/1999 | Morimoto et al. | |
| 6,000,297 A | 12/1999 | Morimoto et al. | |
| 6,416,520 B1 | 7/2002 | Kynast et al. | |
| 6,463,319 B1 | 10/2002 | Bucholz | |
| 6,728,599 B2 | 4/2004 | Wright et al. | |
| 6,836,703 B2 | 12/2004 | Wang et al. | |
| 2002/0122174 A1 | 9/2002 | Hamamatsu et al. | |
| 2003/0013949 A1* | 1/2003 | Moll et al. | 600/407 |
| 2003/0100817 A1* | 5/2003 | Wang et al. | 600/102 |
| 2003/0135203 A1* | 7/2003 | Wang et al. | 606/1 |

OTHER PUBLICATIONS

Article: Rajesh Kumar et al.; "Performance of Robotic Augmentation in Micro-Surgery-Scale Motions"; John Hopkins University (undated).
Article: Rajesh Kumar et al.; Proceedings of the 2000 IEEE International Conference on Robotics and Automation; "Preliminary Experiments in Cooperative Human/Robot Force Control for Robot Assisted Microsurgical Manipulation".
Article: Andrew Bzostek et al.; Submitted for Consideration to MICCAI'99; "Force vs. Deforamtion in Soft Tissue Puncture".
Internet Article: http://www.mein.nagova-u.ac.jp/activity/introduction.html: Cellular Robotic System (CEBOT); Dec. 3, 2002.
Article: Ales Bardorfer et al. Melecon 2000—10$^{th}$ Mediterranean Electrotechnical Conference May 29-31, 2000 Cyprus; "Connecting Haptic Interface With a Robot".
Article: Russell Taylor et al.; International Journal of Robotics Research, 18 (12): 1201-1210 Dec. 1999; "A Steady-Hand Robotic System for Microsurgical Augmentation".

(Continued)

*Primary Examiner* — Khoi Tran
*Assistant Examiner* — Spencer Patton
(74) *Attorney, Agent, or Firm* — Carl H. Pierce; Reed Smith, LLP (57) ABSTRACT

The present invention is a system comprising surgical units and operator interface units configured to provide multiple capabilities within a surgical environment, or within a surgical training environment. The system may provide such capabilities in a modular fashion, such that various functions may be accomplished through the addition or deletion of modules to the system to allow core components to be used to accomplish more than one function.

3 Claims, 10 Drawing Sheets

OTHER PUBLICATIONS

Article: Minyan Shi et al.; Virginia Neurological Institute, Jun. 17, 1997; "Integrated Remote Neurosurgery System".

Web page: http://www.neurosurgery-online.com/abstracts/4803/NURO48030584_abstx.html; Peter D. Le Roux et al; Robot-assisted Microsurgery: A Feasibility Study in the Rat; Dec. 3, 2002.

Web page: http://www.sensable.com/haptics/haptics.html; Haptics Research; Dec. 3, 2002.

Web page: http://www.robotbooks.com/robot-surgeon.htm; "Robots in the News" Dec. 3, 2002.

Web page: http://www.globaltechnoscan.com/21stMar-27thMar01/robot.htm; "Robot-assisted brain surgery is feasible . . . "; Dec. 3, 2002.

Web page: http://www.observer.co.uk/uk_news/story/0,6903,542571.html; Brain surgery by robot gives hope to Parkinson's sufferers; Dec. 3, 2002.

Web page: Cardiothoracic Surgery at the Ohio State University of Nov. 18. 2002; "The DaVinci Robot"; Nov. 18, 2002.

Article: "A Review of Robotics in Surgery," B. Davies, Proc Instn Mech Engrs vol. 214 Part H, Oct. 22, 1999.

Web page: http://www.bmj.com/cgi/content/full "Robots in Operating Theatres" Nov. 12, 2000.

Article: "Is the Robotic Arm a Cost-Effective Surgical Tool?" Karen Dunlap et al.; Aorn Journal, Aug. 1998, vol. 68, No. 2.

Article: "Robots in the Operating Room," Kevin L. Ropp. FDA Consumer/Jul.-Aug. 25, 1993.

Article: "Emerging Technologies for Surgery in the $21^{st}$ Century," Richard M. Satava, Arch Surg/vol. 134, Nov. 1999.

Article: "A Teleoperated Microsurgical Robot and Associated Virtual Environment for Eye Surgery," Ian W. Hunter et al.; Presence, vol. 2, No. 4, Fall 1993, 265-2S0, The Massachusetts Institute if Technology.

Article: "Robotically Driven Interventions: A Method of Using CT Fluroscopy Without Radiation Exposure to the Physician," Stephen B. Solomon et al., RSNA, 2002.

Article: "Quantitative Virtual Reality Enhances Stereotactic Neurosurgery," Patrick Kelly, vol. 80, No. 11, Bulletin of the American College of Surgeons, Nov. 1995.

Article: "NeuRobot: Telecontrolled Micromanipulator System for Minimally Invasive Microneurosurgery—Preliminary Results," Kazuhiro Hongo et al.; Neurosurgery, vol. 51, No. 4, Oct. 2002, 985-988.

Article: "Robot for CT-Guided Stereotactic Neurosurgery," H. Frankhauser et al.; Proceedings of the XIth Meeting of the World Society for Stereotactic and Functional Neurosurgery, Ixtapa, Mexico, Oct. 11-15, 1993.

Article: "Motion Feedback as a Navigation Aid in Robot-Assisted Neurosurgery," Matthias Wapler et al.; Medicine Meets Virtual Reality, IOS Press and Ohmsha, 1998.

Article: "Robotic Three-Dimensional Positioning of a Stimulation Electrode in the Brain," J-L. Hefti et el.; Computer Aided Surgery 3:1-10 (1998).

Article: "New Dimensions of Neurosurgery in the Realm of High Technology: Possibilities, Practicalities, Realities," Michael L. J. Apuzzo, Neurosurgery, vol. 38, No. 4, Apr. 1996.

Article: "A Robot With Improved Absolute Positioning Accuracy for CT Guided Stereotactic Brain Surgery," Yik San Kwon, IEEE.

Article: "Application of Robotics to Stereotactic Neurosugery," Ronald F. Young, Neurosurgical Research, 1987, vol. 9, June.

Article: "ISG Viewing Wand System," Neurosurgery, vol. 34, No. 6, Jun. 1994.

Article: "The First Clinical Application of a Hands-On Robotic Knee Surgery System," M. Jakopec et al., Computer Aided Surgery, 6:329-339 (2001).

Article: "Machining and Accuracy Studies for a Tibial Knee Implant Using a Force-Controlled Robot," Geert Van Ham et al., Computer Aided Surgery, 3:123-133 (1998).

Article: "Anesthesia for Robotic Heart Surgery: An Overview," John M. Murkin, The Heart Surgery Forum #2001-7281, 4(4): 311-314, 2001.

Article: "Current Status and Future Directions in Computer-Enhanced Video- and Robotic-Assisted Coronary Bypass Surgery," W. Douglas Boyd et al., Seminars in Thoracic and Cardiovascular Surgery, vol. 14, No. 1 (Jan. 2002. pp. 101-109).

Article: "Robotic Stabilization That Assists Cardiac Surgery on Beating Hearts," Yoshihiko Nakamura et al.; Medicine Meets Virtual Reality 2001.

The Internet Article: "A Robot That Fixes Hearts," Rob Younge et al. EBSCOhost Full Display, Source U.S. News and World Report, Dec. 25, 2000-Jan. 1, 2001, vol. 129, Issue 25, p. 50.

Article: "Comparison of Robotic Versus Human Laparoscopic Camera Control," Louis R. Kavoussi et al.: The Journal of Urology, vol. 154, 2134-2136, Dec. 1995.

Article: "Feasibility of Robotic Laparoscopic Surgery: 146 Cases," Guy-Bernard Cadiere et al., World Journal of Surgery, 1467-1477, 2001.

Article: "Robot-Assisted Microsurgery: A Feasibility Study in the Rat," Peter D. Le Roux et al., Neurosurgery, vol. 48, No. 3, Mar. 2001.

Article: "Intraoperative Instrument Motion Sensing for Microsurgery," Mario Gomez-Blanco et al., Proceedings of the First Joint BMES/EMBS Conference Serving Humanity, Advancing Technology, Oct. 13-16, 1999, Atlanta, GA, USA.

Article: "An Active Hand-Held Instrument for Enhanced Microsurgical Accuracy," Wei Tech Ang et al., Proceedings of the Third International Conference on Medical Image Computing and Computer-Assisted Intervention, Pittsburgh, PA, Oct. 11-14, 2000.

Article: "Neurological Suite of the Future III," Garnette R. Sutherland et al., Neuroimaging Clinics of North America, vol. 11, No. 4, Nov. 2001.

Internet Article: "Robotic Surgery, Telerobotic Surgery, Telepresence, and Telemonitoring," G.H. Ballantyne, http://link.springer.de/link/service/journals/00464/contents/01/8283/paper/body.html, 2002.

Article: A Force-Reflecting Teleoperated Hand System for the Study of Tactile Sensing in a Precision Manipulation, Robert D. Howe, Proceedings of the 1992 IEEE International Conference on Robotics and Automation, Nice, France, May 1992.

Article: "Computer Guided Microsurgery: Surgical Evaluation of a Telerobotic Arm," B.D. Krapohl, et al., Microsurgery. 21:22-29, 2001.

* cited by examiner

AUGMENTED SURGICAL INTERFACE

RELATED APPLICATIONS

[1] This patent application is a non-provisional application and claims priority from U.S. Provisional Patent Application Ser. No. 60/617,864, filed Oct. 12, 2004, and from U.S. patent application Ser. No. 10/738,359, filed on Dec. 17, 2003, which is a continuation in part of U.S. patent application Ser. No. 10/321,171, filed on Dec. 17, 2002 now U.S. Pat. No. 7,198,630, the entire disclosures of which are incorporated by reference herein as if being set forth in their entireties, respectively.

FIELD OF THE INVENTION

The present invention relates to the field of robotic and computer assisted surgery, and more specifically to equipment and methods for robotic and computer assisted microsurgery.

BACKGROUND

As shown in U.S. Pat. No. 5,943,914 to Morimoto et al., "Master/slave" robots are known in which a surgeon's hand input is converted to a robotic movement. This is particularly useful for motion scaling wherein a larger motion in millimeters or centimeters by the surgeon's input is scaled into a smaller micron movement. Motion scaling has also been applied in cardiac endoscopy, and neurosurgical target acquisition brain biopsy (with a needle) but only in one degree of freedom, for example only for insertion, not for a full range of natural hand movement directions, i.e., not for all possible degrees of natural motion, Cartesian, spherical or polar coordinate systems or other coordinate systems.

Further, in the prior art, surgical robots have been purposefully designed to eliminate the natural hand tremor motions of a surgeon's hand which is about a 50 micron tremor which oscillates with some regularity. The common presumption is that tremor motion creates inaccuracies in surgery. Therefore, robots have been tested which entirely eliminate the surgeon's natural hand tremor. See "A Steady-Hand Robotic System for Microsurgical Augmentation" Taylor et al., *International Journal Of Robotics Research*, 18(12):1201-1210 Dec. 1999, and also see "Robotic-assisted Microsurgery: A Feasibility Study in the Rat" LeRoux et al., *Neurosurgery*, Mar. 2001, Volume 48, Number 3, page 584

The way the primate body handles proprioceptive perception is via sensory feedback scaling (up and down) at the muscular level through the intrafusal fiber system of the Gamma efferent neural circuit. This system responds dynamically to changes in the anticipated muscle performance requirement at any instance by adjusting muscle tone with increased discharging for arousal and attention focusing states, and decrease output for resting and low attention states. The muscle spindle apparatus that does this is located in the muscle body, therefore feedback sensory scaling for muscle positioning, force, length and acceleration is partly programmed at the effector level in "hardware" of the body, i.e., the muscle itself. The evidence indicates a 10 cycle per second refresh rate for the human neurophysiological system in general.

Joint position and fine motor function of the fingers occurs through unidirectional (50% of fibers) and bi-directional (50% of fibers) sensing at the joint structure. This coding is for rotation about an axis, but not for force and no clear speed of rotation feedback.

Cutaneous receptors in the skin code for motion, by modulating higher centers in the thalamus and cerebral cortex. This can be timed to about 75 ms delays before motion occurs, including three neuronal synaptic transmission delays. These sensors are primarily distal to the joint of rotation and distal in the moving effector limb. Finally, the sense of contact is totally discrete from the above motion feedback sensory systems and the neural pathways and integration centers in the deep hemispheres and cerebral cortices function independent of motion to a large degree.

Force reflectance sensing is also known in order to provide tactile or haptic feedback to a surgeon via an interface. See "Connecting Haptic Interface with a Robot" Bardofer et al., Melecon 200—10$^{th}$ Mediterranean Electrotechnical Conference, May 29-31 2000, Cyprus.

However, in testing, all of these techniques ultimately slow down the actual surgery especially when performed in conjunction with a microscope for viewing the operation. The procedure time is typically increased by two to three times. See Robotic-assisted Microsurgery: A Feasibility Study in the Rat" cited above. It is believed that this affect is related to cognitive, perceptive and physiologic discrepancies between a surgeons expectations and the feedback and motions of a surgical robot in use.

Another major design issue regards the choice between locating the surgeon in his normal operating position adjacent to the surgical field or locating the surgeon more remotely from the normal operating position at a terminal with a joystick and viewing screen for example. The prior art elects to locate the surgeon remotely from the traditional operational position about the head and to use monitors to display the operation to the surgeon.

SUMMARY OF THE INVENTION

A system comprising surgical units and operator interface units configured to provide multiple capabilities within a surgical environment, or within a surgical training environment, is described. The system may provide such capabilities in a modular fashion, such that various functions may be accomplished through the addition or deletion of modules to the system to allow core components to be used to accomplish more than one function.

An augmented surgical appliance is also described. The appliance includes a surgical unit, a controller unit for controlling the surgical unit, and at least a first and a second interface unit, the first and second interface units providing force feedback signals to operators of the interface units, where the first and said second interface units are communicably connected to the controller. The surgical unit is communicably connected to the controller, where the controller includes software for transferring control of the surgical unit from the first interface unit to the second interface unit upon receipt of an indication by an operator of the second interface unit that control of the surgical unit should be transferred from the first interface unit to the second interface unit.

Further described is a method for utilizing such an augmented surgical appliance. The method includes the steps of communicably connecting the first and second interface units to the controller, communicably connecting the surgical unit to the controller, transferring control of the surgical unit to the first interface unit, initiating a surgical procedure utilizing the surgical unit, receiving from an operator of the second interface an instruction to transfer control of the surgical unit from the first interface unit to the second interface unit, transferring control of the surgical unit to the second interface unit when an instruction to transfer control of the surgical unit from the first interface unit to the second interface unit is received, and continuing the surgical procedure.

Additionally, a computer readable media, which when executed by a computer implements a process providing control functionality to an augmented surgical appliance, is described. The process includes the steps of transferring control of the surgical unit to the first operator interface unit, receiving from an operator of the second operator interface unit an instruction to transfer control of the surgical unit from the first operator interface unit to the second operator interface unit, transferring control of the surgical unit to said second operator interface unit when an instruction to transfer control of the surgical unit from the first operator interface unit to the second operator interface unit is received, and continuing the surgical procedure.

DETAILED DESCRIPTION OF THE INVENTION

The present invention relates to an augmented surgical appliance, using an operator interface 102 for a surgeon 104 combined with an augmented surgical unit portion 106 for performing surgical procedures. The interface and surgical unit portions are interconnected via a controller 108, which receives input from the interface 102, and converts the input to output performed by the surgical unit 106. Feedback is provided to the interface 102 from the controller 108 in response to parameters measured at the surgical unit 106.

Figure 1:
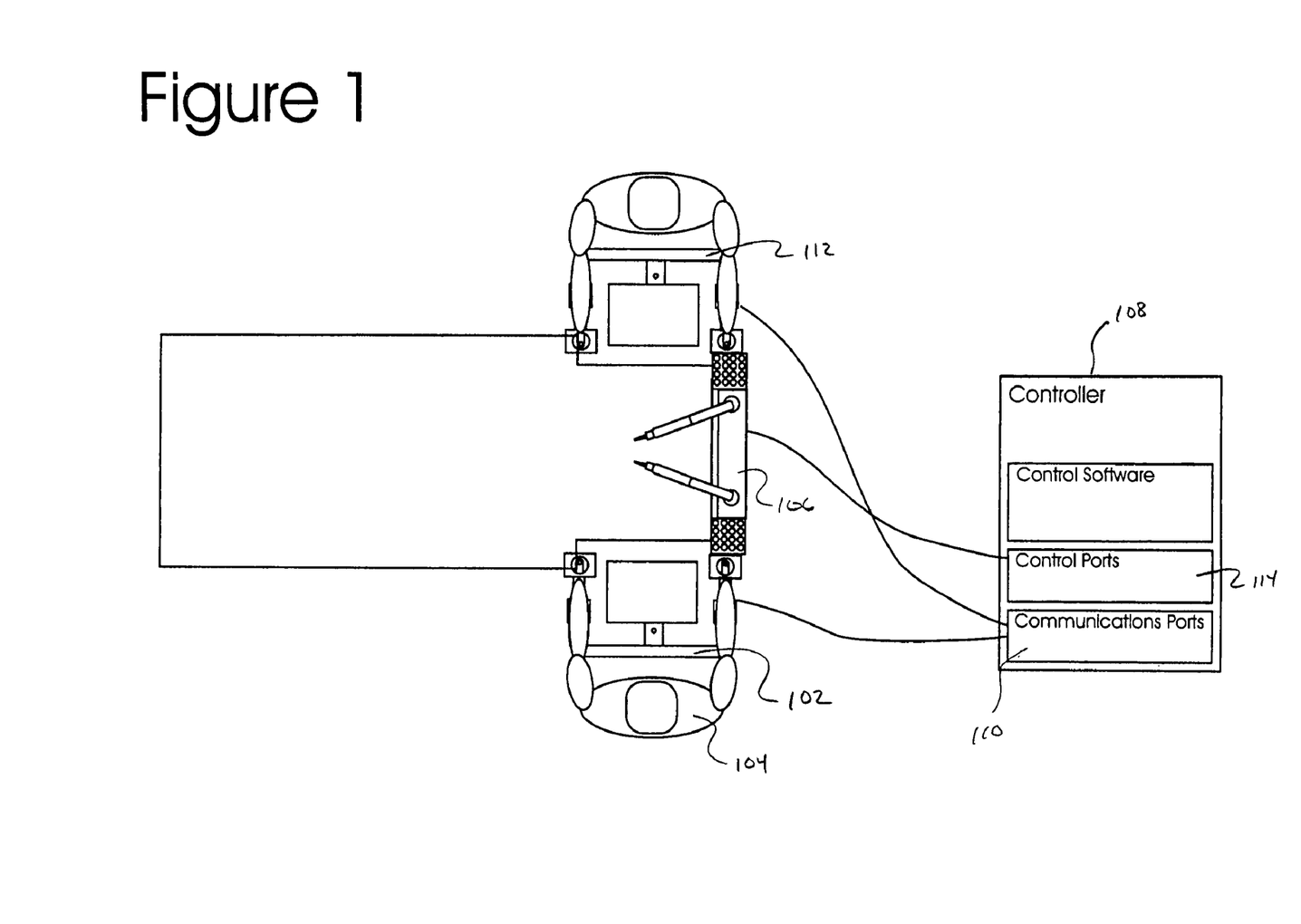
FIG. 1 illustrates an augmented surgical interface according to the present invention, wherein two operator interface units are provided to alternately control a single augmented surgical unit.

As shown in FIG. 1, the controller may be provided with a plurality of communications ports 110 for receiving input from one or more interfaces 102, 112. The controller 108 may also be provided with one or more control ports 114 for providing control signals to the surgical unit 106. As shown in FIG. 1, a single surgical unit 106 may be controlled by a plurality of interface unites 102, 112, where the controller includes functionality for integrating the inputs from the multiple interface units 102, 112 in a coordinated fashion so as to prevent inadvertent signals being transmitted to the surgical unite 106.

In the embodiment as shown in FIG. 1, a single surgical unit 106 may be connected to a control port 114 associated with the controller 108, while an instructor interface 102 and a student interface 112 are connected to communications ports 110 associated with the controller 108.

Figure 2A:
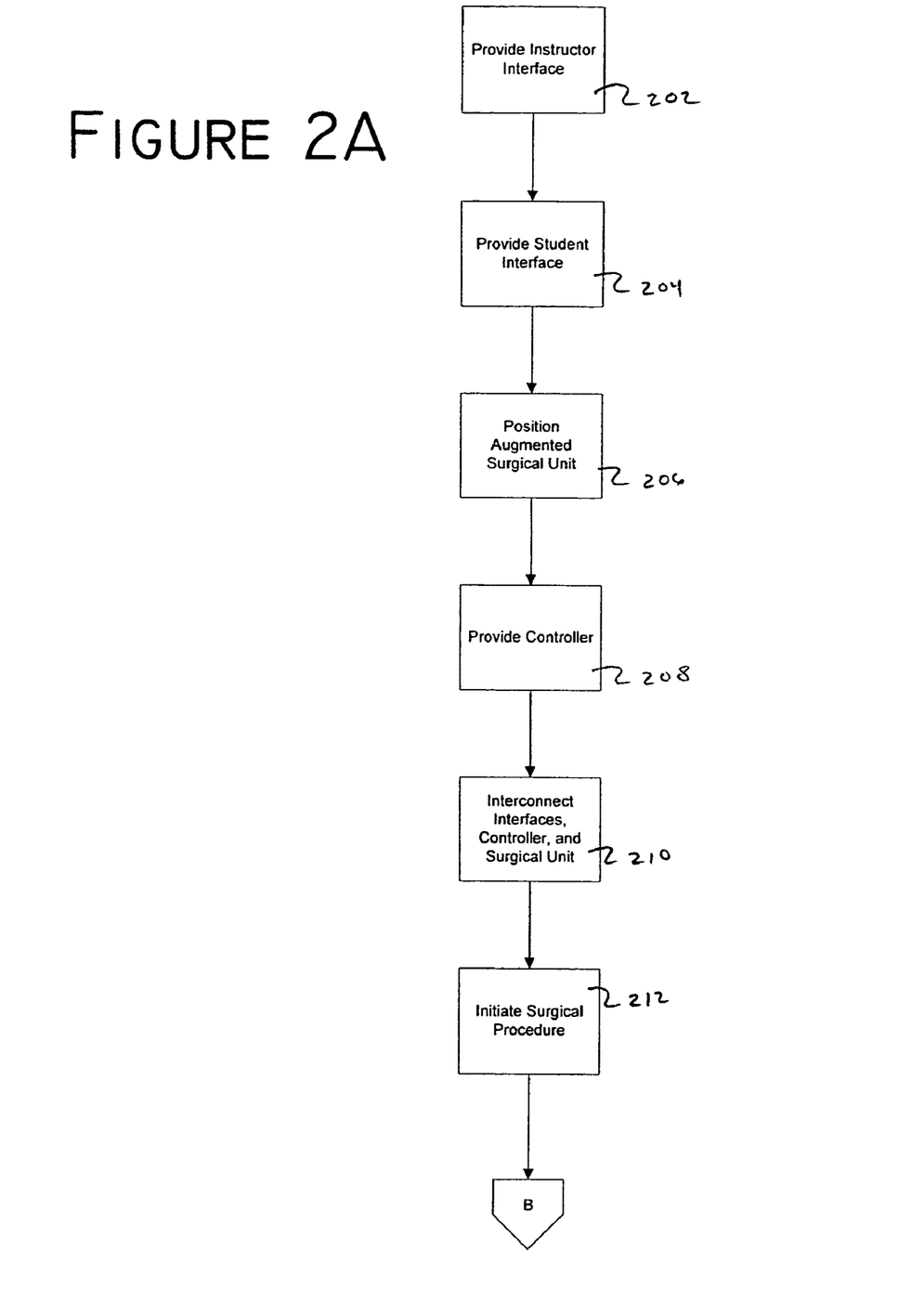
FIG. 2 is a notional process flowchart associated with a process for controlling the system of FIG. 1.
Figure 2B:
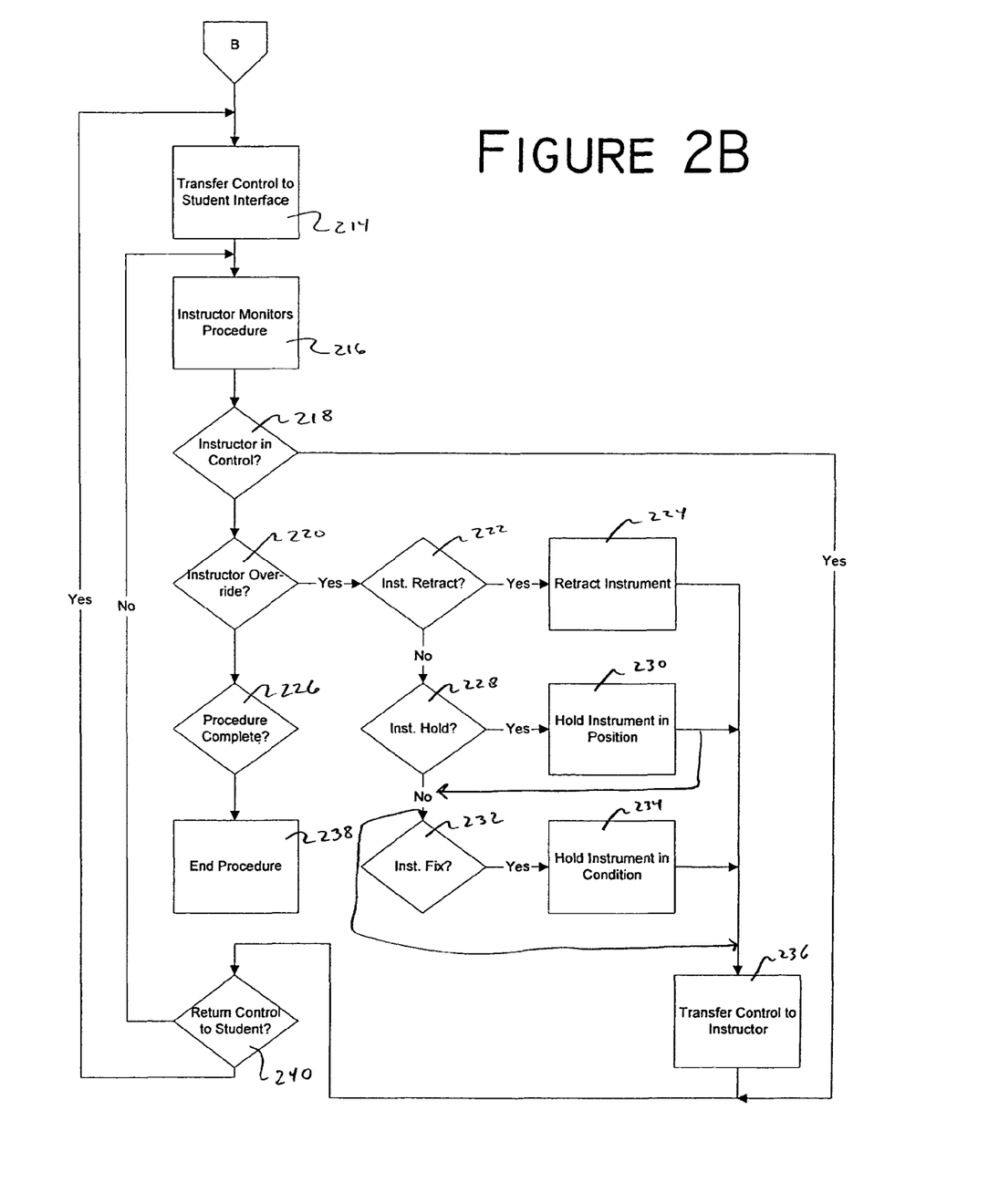

Such a system embodiment allows the instructor interface 102 to provide an instructor 104 to closely observe a surgical procedure, and assume control of the surgical unit 106 either for safety or instructional purposes. Such a process is shown in FIG. 2, wherein an instructor interface and a student interface have been provided 202, 204 in conjunction with a single surgical unit positioned 206 in the surgical field. At the start 212 of the surgical procedure, control of the surgical unit may be transferred 214 to the student interface.

As the surgical procedure proceeds, the instructor may monitor 216 the procedure. If the instructor determines 220 that an over-ride of the student control of the surgical unit is indicated, the instructor may request 220 control of the surgical unit. The transfer may either be a transfer of motion control, may cause a suspension of further motion by locking the motion of the surgical unit, or may cause the surgical unit to translate any tools in use to a safe position.

As it may be desirable to alternately freeze an instrument in position, hold an instrument in an as deployed condition, or cause the instrument to retract to a safe position, it may first be determined 222 whether the instructor desires the instrument to be retracted. If the instructor desires the instrument to be retracted, the controller may command 224 retraction of the instrument to a safe position. If the instructor does not desire to have the instrument retracted, it may then be determined 228 whether the instructor desires the instrument to be held in place. If the instructor desires the instrument to be held in place, the controller may command 230 that the instrument be held at a location until released by the instructor. Additionally, where an instrument is being held in place 230, it may be determined 232 whether the instrument should be fixed as to condition (i.e., open or closed for a forceps), and if it is determined that it is desired to fix the instrument in a condition, the controller may command 234 that the instrument be fixed as to condition until released to the operator. Once the transfer parameters have been determined and commanded by the controller, control of the surgical unit may be transferred 236 to the instructor. This determination of transfer parameters may be extended to multiple effectors/instruments in use, i.e., parameters may be obtained for both an effector associated with a right hand control and for an effector associated with a left hand control. Transfer parameters may also be preconfigured, such as should an instructor require a rapid transfer of control, the instruments/effectors could be preconfigured to transfer as free, to a retracted position, to a hold position, and/or a fixed condition.

The procedure may continue with the instructor in control until the instructor determines 240 that control should be transferred back to the student, at which point control may be transferred 214 to the student. Such transfer may additionally implement retraction of instruments in use, position hold for instruments in use, and a condition fix for instruments in use.

Figure 3:
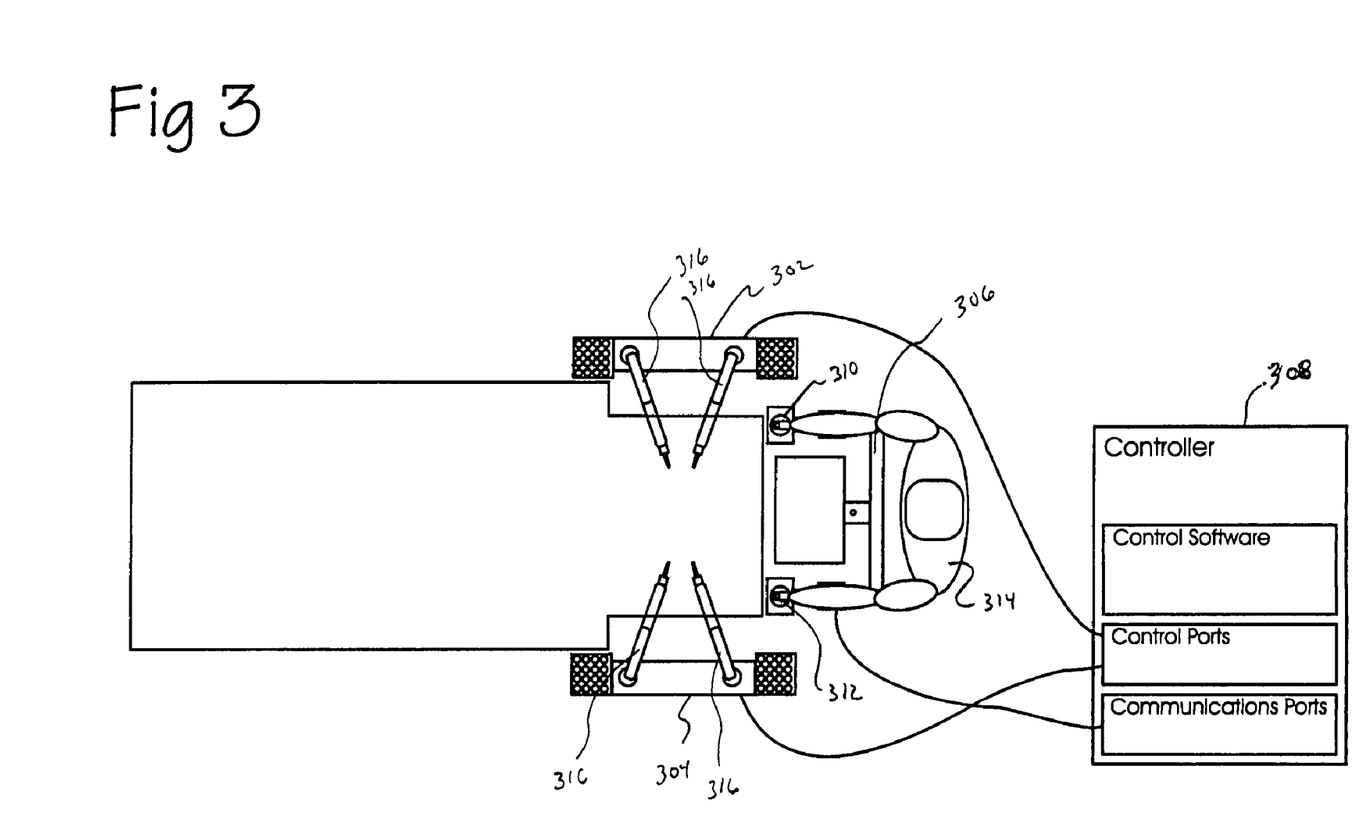
FIG. 3 illustrates an augmented surgical interface system according to the present invention, wherein two augmented surgical units are controlled concurrently by a single operator interface unit.

As shown in FIG. 3, the system may be configured in the operating room to include two surgical units 302, 304, associated with a single interface unit 306 via a controller 308. The interface unit 306 may typically have two hand controllers 3310, 312, corresponding to the left and right hands (not shown) of an operator 314. The surgical units 302, 304 may typically have more than one effector 316 per surgical unit 302, 304 (two effectors per unit are shown), such that an operator 314 has four (4) possible effectors to control from two hand controllers 310, 312. The use of multiple effectors allows a larger tool set to be available to the operator 314.

Figure 4A:
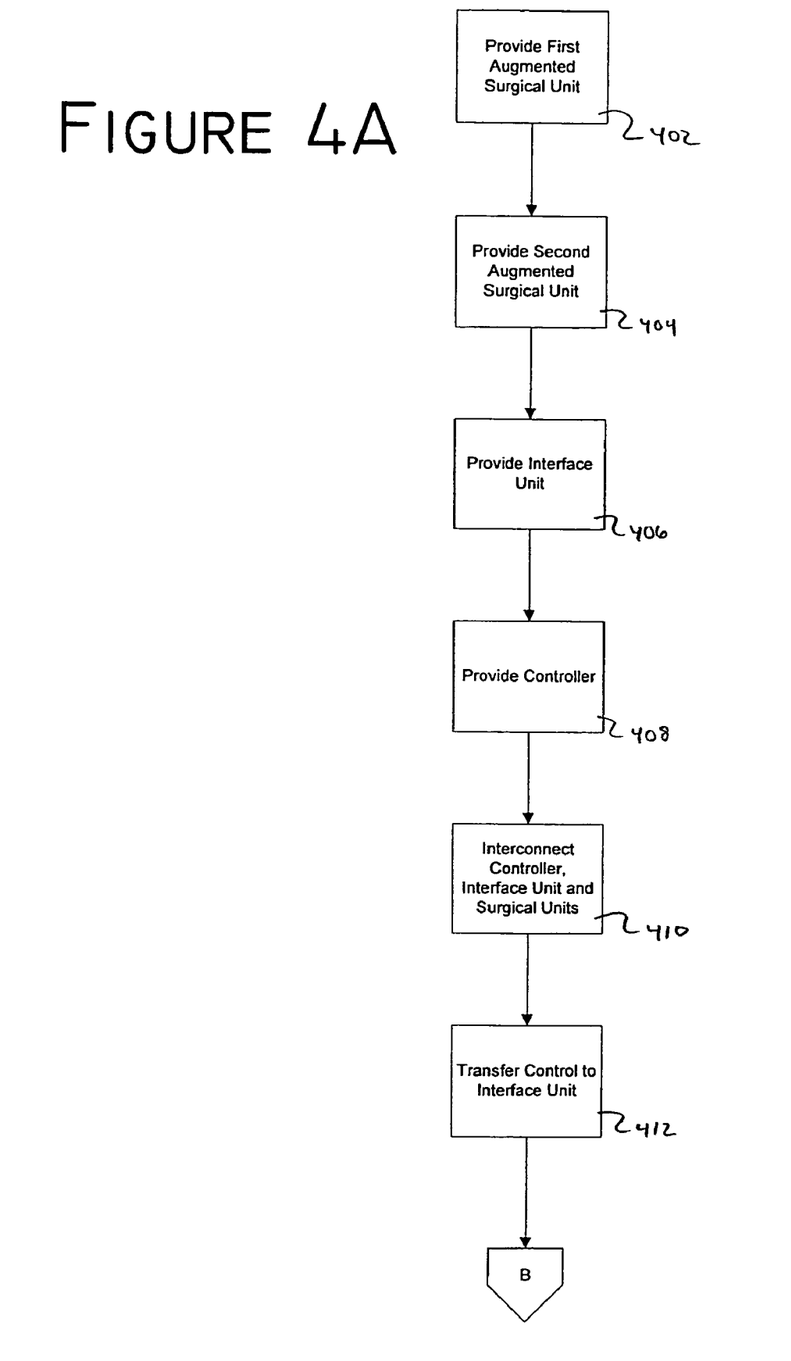
FIG. 4 illustrates a notional process flowchart associated with a process for controlling the system of FIG. 3.
Figure 4B:
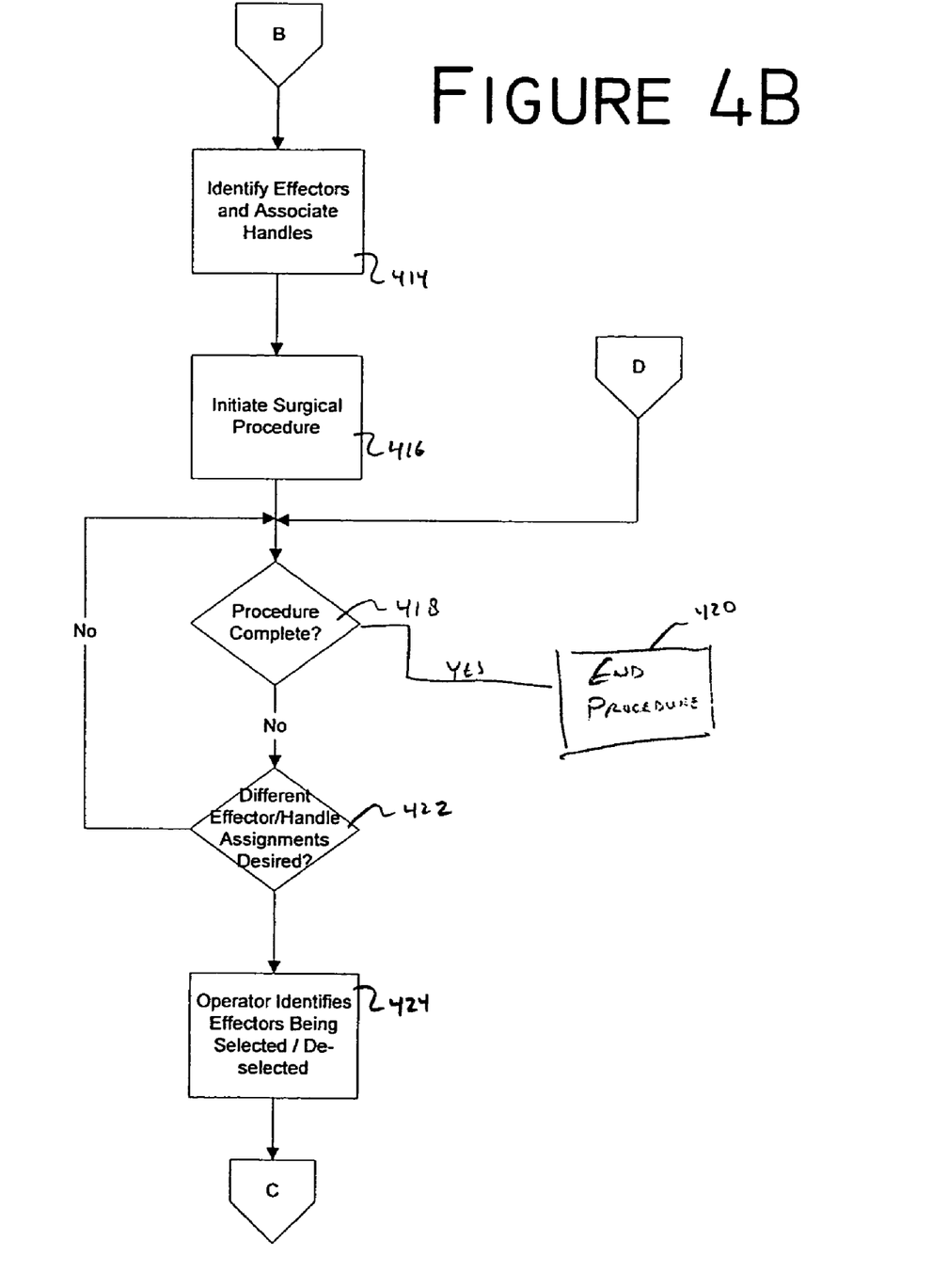
Figure 4C:
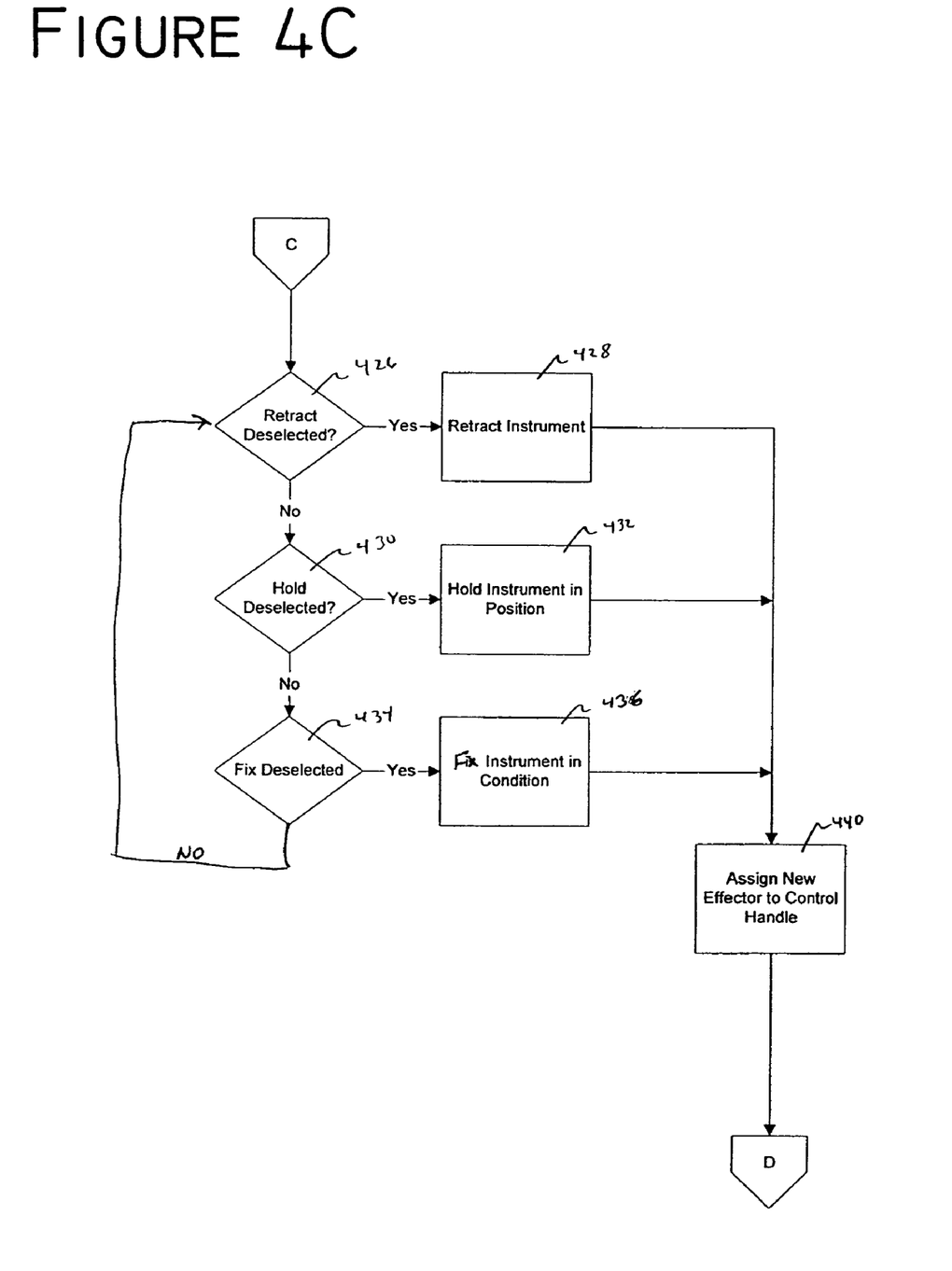

As shown in FIG. 4, the use of a greater number of effectors than hand controllers may be accomplished using the illustrated process. The surgical environment may be provided with an inter unit 406, as well as be provided 402, 404 with first and second surgical units. The interface and surgical units may be communicably connected 410 to a controller. Control of the surgical units may be transferred 412 to the interface, at which point the operator may select 414 effectors and associate them with hand controllers. For example, an effector on the first surgical unit may be associated with the right hand controller, while an effector associated with the second surgical unit may be associated with the left hand controller. Such association may not only provide control authority over the given effector by a selected hand controller, it may also cause the controller to apply feedback parameters associated with the selected effector to the hand controller.

Once the desired effector and hand controller associations have been selected 414, the surgical procedure may be initiated 416. If the operator determines 422 during the procedure that different effector assignments are desired (i.e., use of a new effector or re-assignment of an effector in use to a different hand controller is desired) the operator may identify 426 the new effector/hand control assignment to the controller.

The position and condition of the effector will typically be of significance, such as where a tool for retracting flesh is being deselected. If the retractor were erroneously retracted, it could cause complications of the surgical procedure. Accordingly, it may be desirable to fix the effector in a position to allow a tool in use on the effector to remain in use after the effector is deselected. Alternately, it may be desirable to have the tool automatically retracted to a position outside of the surgical field. The surgeon operating the interface may thus indicate which response is desired. Additionally, where tools may have multiple degrees of freedom, such as a forcep tool having both position and clamping conditions, the operator may further indicate whether it is desired that the tool remain in the additional conditions, such as clamped or unclamped for a forcep tool. Again, the transfer condition of an instrument may be defined by the operator. If it is determined 426 that the operator desires an effector/instrument to be retracted prior to the transfer, effector/instrument may be retracted 428. If it is determined 430 that the operator desires that a de-selected effector/instrument be held in position, the controller may issue commands to hold 423 the effector/instrument in position. Finally, if it is determined 434 that the operator desires that an effector/instrument be fixed as to condition, the controller may issue commands to fix the instrument in a given condition. Holding an instrument in position may be included when an effector/instrument is fixed as to position. If neither retract, hold, and/or fix as indicated, the operator may be queried to determine which condition the de-selected instrument should be left in. Once the condition of the deselected effector/instrument has been determined and accomplished, control of a selected effector/instrument may be assigned 440 to an identified control handle, and the surgical procedure may continue.

Although the flowchart illustrates only a single cycle of a new effector/hand controller assignment occurring, it is contemplated that multiple reassignments may occur during a single surgical procedure.

Figure 5:
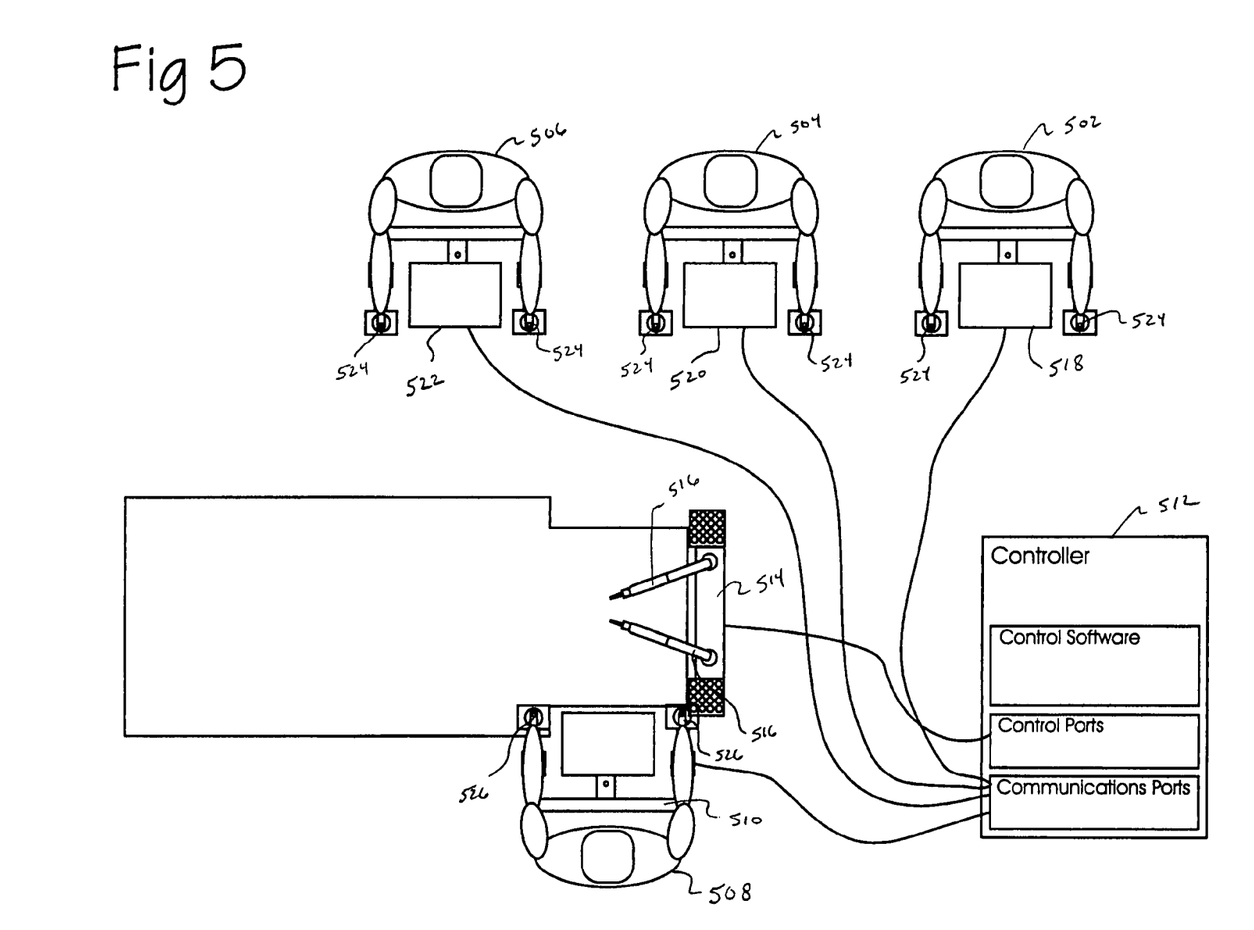
FIG. 5 illustrates an augmented surgical interface system according to the present invention, wherein a plurality of repeater interfaces are provided to allow operators in training to follow through a surgical procedure in process.

As shown in FIG. 5, the augmented surgical interface system may further be implemented to allow one or more operators in training 502, 504, 506 to follow through a surgical procedure being performed by a first surgeon 508. The surgeon 508 may be provided with an interface unit 510 connected to a controller 512. A surgical unit 514 having one or more effectors 516 may additionally be connected to the controller.

Repeater interfaces 518, 520, 522 may be provided to allow operators in training 502, 504, 506 to follow through as the first surgeon 508 performs a procedure. In such a situation, the repeater interfaces would not have control authority over the surgical unit 514, however would receive display and feedback parameters from the controller 512, such that control handles 524 on the repeater interfaces 518, 520, 522 would mirror the positioning of the control handles 526 on the operator interface 510. Accordingly, the feedback systems utilized in the interface units as described previously would cause the control handles 524 to mirror the motions of the first surgeon's control handles 526. Additionally, the provision of display units 528 on the repeater interfaces 518, 520, 522 would allow the operators in training 502, 504, 506 to also see the visual presentations being provided to the first surgeon 508.

The repeater interfaces 518, 520, 522 may be the same as the interface unit 510, with the controller 512 being used to prevent the repeater interfaces 518, 520, 522 from having any control authority over the surgical unit 514. The use of common interface units may reduce the cost of implementing such a system on a hospital, such that where a hospital procures surgical units for more than one operating theater, the associated interface units may be aggregated in a single operating theater for a procedure which is to be followed through by operators in training, without the hospital having to procure additional equipment.

Figure 6:
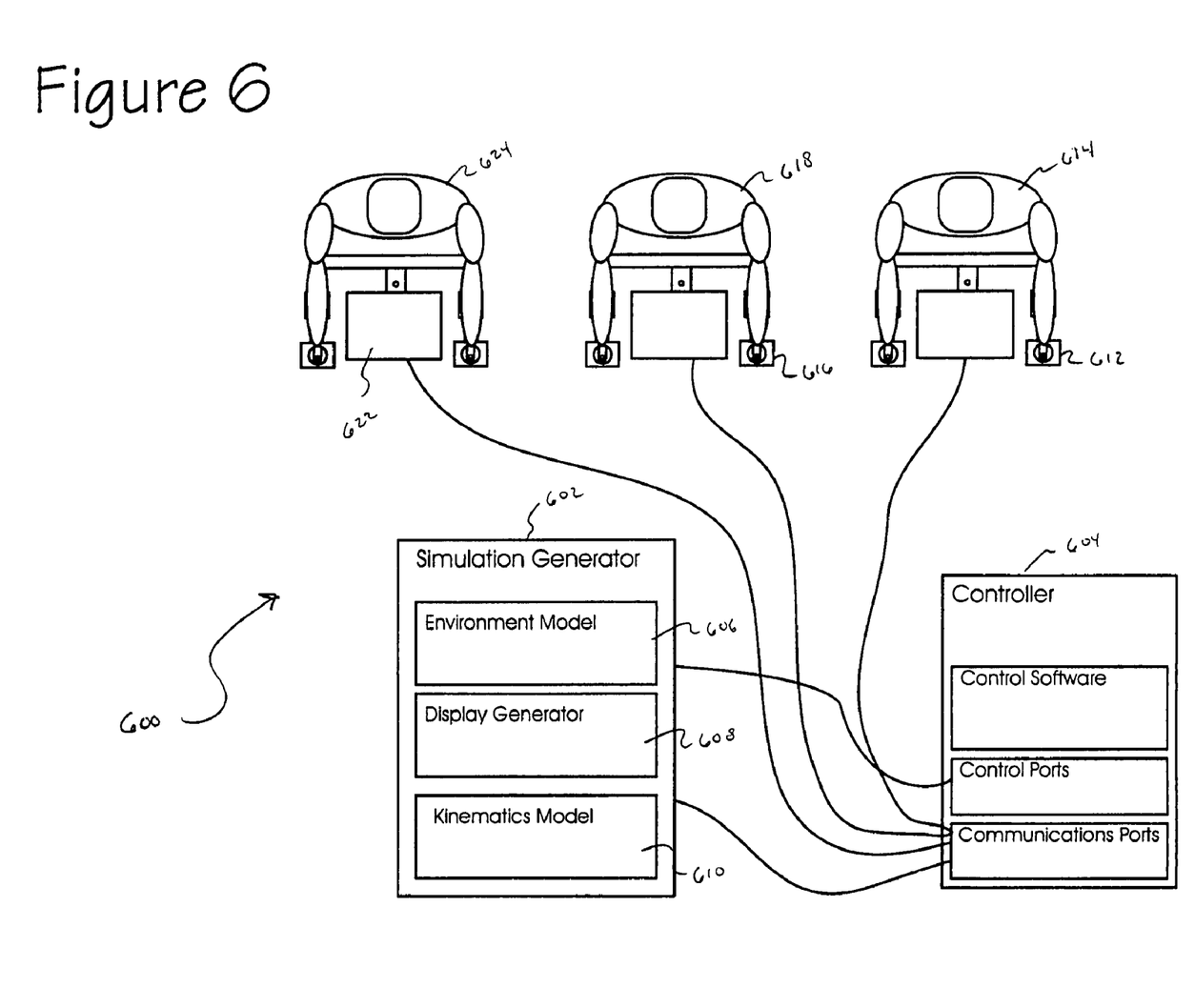
FIG. 6 illustrates an augmented surgical interface system configured to provide a simulated surgical procedure, wherein the system includes a simulation generator, a first interface unit, a second interface unit, and repeater interface unit.

As shown in FIG. 6, the modular nature of the controller 604, surgical unit, and interface units also lend themselves to aggregation to form a simulator system 600. A simulation generator 602 may be connected to a controller 604. The simulation generator 602 may be provided with an environment model 606 for defining expected responses as a tool moves within a simulated surgical field. Such an environment model 606 may include parameters defining tissue position and consistency, as well as tissue response parameters to various surgical instruments which may be encountered during a simulated surgical procedure. The simulation generator 602 may further be provided with a display generator 608 for generating a simulated display of the surgical field, including tissue and tool positioning, as well as indicators and feedback that would be provided to a surgeon during a procedure.

Finally, the simulation generator may further be provided with a kinematics model 610 that models the kinematic response of surgical instruments within the surgical field, such as contact information, acceleration forces and other motion forces which would be encountered during an actual procedure. The output of the simulation generator may be provided to the controller, such that the controller is provided with signals which would be consistent with the signals transmitted to the controller during an actual procedure. A first interface unit 612 may be designated as the controlling interface unit, such that commands provided by an operator 614 of the first interface unit would be used to provide command parameters for a simulated surgical procedure. A second interface unit 616 could be provided for a supervising surgeon or operator 618, such that the training system of FIG. 1 could be implemented in a simulated environment, such as may be desired to familiarize an operator in training 620 with the hand off procedures.

Finally, a third interface unit 622 may also be provided to allow a second operator in training 624 to follow though the simulated procedure, or to step in upon the directions of the supervising surgeon or operator 618. The third interface may alternately be limited such that control authority could not be transferred to the third interface unit 622, effectively rendering the third interface unit to be a repeater interface unit.

Figure 7:
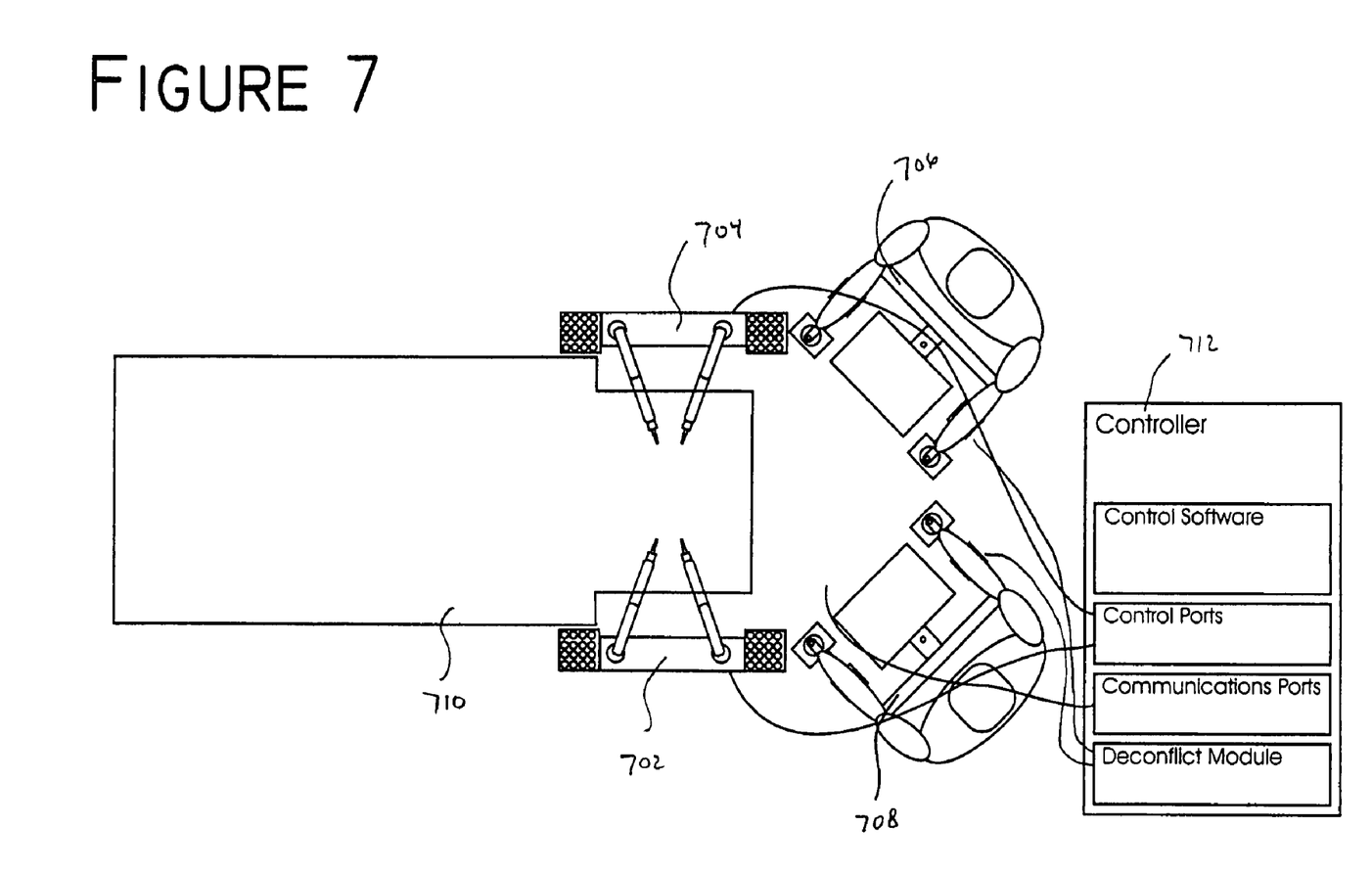
FIG. 7 illustrates an augmented surgical interface system according to the present invention, wherein two operator interface units are provided to concurrently control two augmented surgical units via a controller incorporating functionality to deconflict motions of effectors associated with the surgical units.

As shown in FIG. 7, it may be desired to utilize multiple surgical units 702, 704 in conjunction with multiple interface units 706, 708 during a surgical procedure. In such a situation, the ability to prevent interference between instruments associated with the different surgical units 702, 704 may be of paramount importance.

The position of tools within the surgical field may be modeled as a function of the position of the surgical units to a fixed reference, such as the surgical table. The use of such referencing was discussed previously. By indexing both surgical units 702, 704 to the surgical table 710, the resultant position of the surgical instruments could be determined by the controller 712 as a function of the position of the effectors to which the instruments are attached, as well as predetermined knowledge of the instruments themselves.

Although the position of the tools is important in preventing interference between the tools, predictive analysis of the motion of the instruments themselves may provide a more effective function for the operators. The projected position of the tools may be based on the present motion and speed of the instruments, such that an increasing value can be determined indicating the likelihood of interference between the instruments. Such a value may be increased the sooner an interference may occur, i.e., a likely interference that will not occur for a longer period of time will be assigned a lower value than a likely interference which will occur sooner.

An indication of the likelihood of contact may be presented to one or both of the operators during a procedure with multiple interface units. The indicator may be a visual or audible warning to the operators. Alternately, the controller may impose a scale function to the motion of the instruments as a function of the likelihood of the interference. For example, a velocity component of a commanded motion of an instrument may be reduced by an increasing factor the higher the likelihood of an interference. Thus, minimal scaling of the motion command would occur where the interference was of a lower likelihood, i.e., not expected to occur for a given amount of time. As the likelihood of the interference is expected to occur sooner, the scaling of the motion command may be increased to further slow the motion of the instrument, thus reducing the likelihood of an interference, as well as signaling the operator of the likelihood of the interference.

Other variations and modifications of the present invention will be apparent to those of skill in the art, and it is the intent of the appended claims that such variations and modifications be covered. The particular values and configurations discussed above can be varied and are cited merely to illustrate a particular embodiment of the present invention and are not intended to limit the scope of the invention. It is contemplated that the use of the present invention can involve components having different characteristics as long as the principles of the invention are followed.

What is claimed is:

1. An augmented surgical appliance comprising:
    a plurality of surgical units, said surgical units each comprising at least one effector for applying a surgical tool to a patient's tissue;
    at least one controller unit; and
    an interface unit, said interface unit having a plurality of hand controllers for receiving positioning inputs from an operator, said interface unit further providing force feedback signals to an operator of said interface unit,
    wherein said plurality of surgical units are communicably connected to said controller;
    wherein said interface unit is communicably connected to said controller; and
    wherein said controller comprises software for transforming input received from said interface unit into control signals communicable to said surgical units, and wherein said software further comprises functionality to allow an operator to associate desired effectors with desired hand controllers and receive an indication from said operator that an effector and/or instrument associated with a surgical unit should be moved to a retracted position when the effector and/or instrument is no longer associated with a hand controller.

2. A method for utilizing an augmented surgical appliance having more effectors than hand controllers, comprising the steps of:
    providing an interface unit, said interface unit having at least one hand controller, said hand controller receiving positioning commands from an operator of said interface unit and providing force and positioning feedback to said operator;
    providing at least one surgical unit, said at least one surgical unit having a plurality of effectors, said plurality of effectors having at least one more effector than hand controllers;
    providing a controller unit for receiving positioning commands from said interface unit and for generating control signals for said plurality of effectors, said controller unit further generating control signals for said interface unit for providing force and positioning feedback;
    communicably connecting said interface unit to said controller;
    communicably connecting said surgical unit to said controller;
    transferring control of said surgical unit to said interface unit;
    receiving from an operator of said interface unit information identifying desired associations between said at least one hand control and said effectors, said association identifying a single effector to be associated with a given hand controller;
    initiating a surgical procedure utilizing said surgical unit;
    receiving from said operator a new desired association between said at least one hand control and said effectors, said association identifying a single effector to be associated with a given hand controller, and further comprising the step of determining from said operator whether said operator desires to have a deselected effector move to a retracted position; and
    continuing said surgical procedure.

3. A computer readable media, which when executed by a computer implements a process providing control functionality to an augmented surgical appliance, said surgical appliance having an interface unit, said interface unit having at least one hand controller, said hand controller receiving positioning commands from an operator of said interface unit and providing force and positioning feedback to said operator, said surgical appliance further having a surgical unit, said first surgical unit having a plurality of effectors, said plurality of effectors having at least one more effector than hand controllers, said surgical appliance further having a controller unit for receiving positioning commands from said interface unit and for generating control signals for said plurality of effectors, said controller unit further generating control signals for said interface unit for providing force and positioning feedback, said process comprising the steps of:
    transferring control of a surgical unit to an interface unit;
    receiving from an operator of said interface unit information identifying desired associations between said at least one hand control and said effectors, said association identifying a single effector to be associated with a given hand controller, and further comprising the step of determining from said operator whether said operator desires to have a deselected effector move to a retracted position;
    initiating a surgical procedure utilizing said surgical unit; and
    receiving from said operator a new desired association between said at least one hand control and said effectors, said association identifying a single effector to be associated with a given hand controller.

* * * * *